United States Patent [19]

Nash et al.

[11] 4,286,099

[45] Aug. 25, 1981

[54] SULFOLENE HYDROGENATION

[75] Inventors: Martin E. Nash; Edward E. Huxley, both of Borger, Tex.

[73] Assignee: Phillips Petroleum Company, Bartlesville, Okla.

[21] Appl. No.: 120,811

[22] Filed: Feb. 12, 1980

[51] Int. Cl.$^3$ ........................................... C07D 333/48
[52] U.S. Cl. ..................................................... 549/87
[58] Field of Search .......................... 568/881; 549/87

[56] References Cited

U.S. PATENT DOCUMENTS

| | | | |
|---|---|---|---|
| 2,578,565 | 12/1951 | Mahan et al. | 549/87 |
| 3,152,144 | 10/1964 | Middlebrook | 549/87 |
| 3,417,103 | 12/1968 | Warner | 549/87 |
| 3,514,469 | 5/1970 | Phillips et al. | 549/87 |
| 3,928,385 | 12/1975 | Huxley | 549/87 |

OTHER PUBLICATIONS

Ellis, "Hydrogenation of Oils", 2nd ed., 1919, p. 161.

*Primary Examiner*—Alan Siegel

[57] ABSTRACT

Prior to hydrogenation to produce sulfolane, a sulfolene feed containing sulfur-containing catalyst poisons is contacted with used and/or at least partially spent Raney nickel catalyst under conditions which substantially remove and/or render innocuous the catalyst poisons. The pretreatment removes sulfur dioxide and polymeric sulfones from the sulfolene which would otherwise contaminate and deactivate the fresh catalyst employed in the hydrogenation.

15 Claims, No Drawings

SULFOLENE HYDROGENATION

This invention relates to the production of sulfolane. In accordance with another aspect, this invention relates to an improved process for the catalytic hydrogenation of sulfolene, such as 3-sulfolene to sulfolanes. In accordance with another aspect, this invention relates to a process for the pretreatment of a sulfolene containing feed to remove and/or render innocuous catalyst poisons present in the feed by contact with at least partially spent and used Raney nickel catalysts. In accordance with another aspect, this invention relates to a process for removing and/or rendering innocuous sulfur dioxide and other sulfur compounds present in sulfolene feeds for hydrogenation of sulfolene to sulfolanes by pretreatment with at last partially spent Raney nickel catalysts in the presence of a tertiary amine followed by hydrogenation in the presence of an active hydrogenation catalyst. In accordance with another aspect, this invention pertains to the treatment of a sulfolene compound prior to its hydrogenation to a sulfolane compound by contacting with at least partially used or spent Raney nickel catalysts which have been previously employed in hydrogenation of a sulfolene compound.

Sulfolane compounds are useful for a variety of purposes, such as in pesticidal compositions, intermediates in the production of other organic chemicals, selective solvents to separate aromatic hydrocarbons from petroleum fractions and the like. The sulfolane compounds are generally prepared by the catalytic hydrogenation of the corresponding sulfolene compounds. These sulfolene compounds are generally prepared by reaction of sulfur dioxide with a sulfolene precursor such as a conjugated diene, thus giving a sulfolene compound which generally contains minor amounts of sulfur dioxide as well as polymer generally described as "polysulfone". In the subsequent hydrogenation of the sulfolene compounds to sulfolane compounds, the sulfur dioxide and polysulfones present therein poison or coat the hydrogenation catalysts and significantly reduce the activity thereof.

The prior art has recognized the problems associated with hydrogenation of sulfolene compounds containing sulfur dioxide and polysulfone. Several prior art references teach techniques for reducing the amount of or scavenging the sulfur dioxide and/or polysulfone in the sulfolene compounds. In U.S. Pat. No. 3,152,144, sulfolene compounds are treated with hydrogen peroxide prior to hydrogenation in order to convert sulfur dioxide to sulfur trioxide. In U.S. Pat. No. 3,417,103, sulfolene compounds are subjected to reduced pressure to remove some sulfur dioxide and then treated with calcium oxide or hydroxide or magnesium oxide or hydroxide to convert the remaining sulfur dioxide to partially insoluble sulfite salts which can be removed by filtration. In U.S. Pat. No. 3,514,469, sulfolene compounds are treated with alkali metal peroxides in order to convert the sulfur dioxide to the soluble sulfate salt which remains in solution during the hydrogenation step. U.S. Pat. No. 3,928,385 discloses the use of a tertiary amine to treat sulfolene compounds prior to hydrogenation in order to inhibit polymer formation during hydrogenation.

Accordingly, an object of this invention is to provide an improved process for the hydrogenation of sulfolenes.

Another object of this invention is to provide a pretreatment step to remove and/or render innocuous catalyst poisons present in the hydrogenation feed converting sulfolenes to sulfolanes.

A further object of this invention is to provide a process that effectively scavenges residual sulfur-containing compounds in sulfolene feeds so as to increase conversion during hydrogenation and, at the same time, require less catalyst.

Further aspects, as well as the several advantages, of this invention will become apparent to those skilled in the art from the following description and appended claims.

In accordance with the invention, a process is provided which comprises contacting at least one sulfolene compound containing catalyst poisons with hydrogen in the presence of at least partially spent and/or used metal hydrogenation catalysts under conditions sufficient to remove and/or render innocuous the catalyst poisons and then subjecting the pretreated feed to hydrogenation with an active hydrogenation catalyst under hydrogenation conditions sufficient to effectively convert sulfolene compounds to sulfolane compounds.

In accordance with one embodiment of the invention, a sulfolene feed containing sulfur-containing catalyst poisons is pretreated by contacting with at least partially spent and/or used Raney nickel catalysts which has been previously employed in hydrogenation of a sulfolene compound under conditions sufficient to remove and/or render innocuous the catalyst poisons prior to hydrogenation.

In accordance with another embodiment of the invention, pretreatment of the sulfolene-containing feed, also containing catalyst poisons, is carried out in the presence of a tertiary amine.

The present invention avoids the addition of any materials not normally employed in a sulfolene hydrogenation, thus avoiding subsequent product contamination or further complicated purification procedures. By employing as a treating agent a previously used Raney nickel catalyst which retains some degree of scavenging activity, the sulfur dioxide contained in the sulfolene compound reacts with the active scavenging sites and, hence, is substantially removed from solution and the polysulfones which are present in the sulfolene compound become associated with the spent catalyst particles as a coating thereon. Thus, materials known to decrease catalyst activity in a hydrogenation of sulfolene compounds are substantially removed prior to the hydrogenation process, and thereby markedly greater catalyst activity, efficiency, and life-time are realized.

The term "sulfolene compound" as employed herein defines generically the unsubstituted and substituted unsaturated compounds comprising or containing a sulfolene nucleus, i.e., a 5-membered ring of 4 carbon atoms and a sulfur atom with a single olefinic linkage between two adjacent carbon atoms of said ring, and two oxygen atoms, each of which is directly attached to said sulfur atom. Thus, the generic term "sulfolene compound" covers the unsubstituted and substituted sulfolenes, namely, the 3-sulfolenes having a general structure

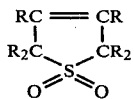

and the 2-sulfolenes having the structure

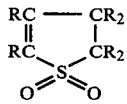

wherein each R is individually selected from the group consisting of hydrogen, hydrocarbon radicals, heterocyclic radicals, and inorganic radicals, and combinations thereof which do not interfere with the hydrogenation reaction. Those compounds wherein each R is individually selected from the group consisting of hydrogen and hydrocarbon radicals having 1 to 8 carbon atoms are presently preferred. Suitable hydrocarbon radicals include alkyl, aryl, cycloalkyl, and combinations thereof.

The following representative sulfolene compounds are suggested to those skilled in the art as being operable in this invention: 3-sulfolene, 2-sulfolene, 3-methyl-2-sulfolene, 2-methyl-3-sulfolene, 3-methyl-3-sulfolene, 2,4-dimethyl-2-sulfolene, 2,4-dimethyl-3-sulfolene, 3-ethyl-3-sulfolene, and their homologues, as well as other sulfolene compounds, and mixtures thereof.

Similarly, the term "sulfolane compound" as used herein refers to a hydrogenated sulfolene compound, which may be either substituted or unsubstituted. The structure formula of the sulfolane compounds is

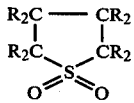

wherein each R is as defined hereinabove, with at least one R on each of two adjacent carbon atoms being hydrogen.

The inventive treatment is preferably carried out with the sulfolene compound in the liquid state, for example, by maintaining it above its melting point (but below its thermal decomposition temperature) or in solution in a suitable diluent such as water, benzene, dioxane, alcohols, such as methyl, ethyl, isopropyl or tertiary butyl alcohol, the sulfolane compound itself and the like. The amount of diluent used can vary and generally will be in the range of about 10 to about 75 percent by volume of total solution, preferably about 30 to about 50 percent by volume. The use of a diluent permits better control over the temperature of the rapid and exothermic reaction.

The reaction temperatures and pressures can vary over wide ranges. In fact, any temperature is operable at which the reaction mixture is liquid and which is below that at which the materials decompose. The treatment of sulfolene compounds with spent Raney nickel catalyst generally occurs in the temperature range of about 10° to about 70° C. and preferably in the range of 50° to about 65° C. Treatment pressure is generally in the range of about 100 to about 7,000 kPa and preferably in the range of about 250 to about 400 kPa with hydrogen being the pressurizing gas. Treatment times, of course, will depend upon the temperatures and pressures employed, but will generally be in the range of about 10 minutes to about 3 hours, and preferably 30 minutes to about 1 hour. It is especially preferable to employ conditions of temperature and pressure which are the same as those subsequently employed in the hydrogenation process.

The treating agent employed in the treatment of sulfolene compounds is used or spent Raney nickel catalyst which has been previously employed in the hydrogenation of sulfolene compounds. Thus, used Raney nickel catalyst which has insufficient catalytic activity to be commercially useful in further hydrogenation reactions but which still exhibits an observable degree of scavenging activity is useful in this invention. It will be recognized by one skilled in the art that used Raney nickel catalyst from hydrogenation of sulfolene compounds will have a considerable portion of the catalyst surface poisoned by previous reaction with sulfur dioxide and will have a considerable portion of the catalyst surface covered with a coating of polymeric by-product herein referred to as polysulfone.

The amount of spent Raney nickel catalyst employed in the treatment of sulfolene compounds can vary greatly depending, of course, upon the amount of scavenging activity, as well as the treatment conditions employed. Generally, however, the treating agent is employed in amounts ranging from about 0.1 to about 100 parts by weight treating agent per 100 parts by weight sulfolene compound, and preferably in the range of about 2.5 to about 20 parts by weight per 100 parts by weight of sulfolene compound.

It will be recognized by those skilled in the art that the scavenging activity which remains after use of the Raney nickel catalyst in sulfolene hydrogenation is dependent not only upon the amount of catalyst sites poisoned by reaction with sulfur dioxide or coated with polysulfone, but also, upon the subsequent treatment of the catalyst during recovery of the thus-produced sulfolane compounds. Exposure of the spent catalyst to air and other catalyst-deactivating agents can drastically reduce the scavenging activity of the spent catalyst. Thus, while the spent Raney nickel catalyst useful in the treatment of this invention is not dependent upon any particular pre-treatment or past history other than use in a sulfolene hydrogenation so long as observable scavenging activity remains, it is preferred that the spent catalyst is maintained under hydrogen atmosphere from the time of its removal from the previous sulfolene hydrogenation to its use in the inventive treatment of a sulfolene compound and especially preferred that the spent catalyst be maintained under positive hydrogen pressure ranging from about 100 kPa to about 1,000 kPa.

Those reasonably skilled in the art will recognize that employing the above-described treatment conditions and the spent Raney nickel catalyst which retains some scavenging activity will result in the hydrogenation of a portion of the sulfolene compound to sulfolane compound during the treatment step. Such hydrogenation which can occur will be additive to the total hydrogenation which is subsequently carried out and thus will not be detrimental to the practice of this invention. It is recognized that the degree of hydrogenation of sulfolene compound which occurs during the treatment step can be an approximate indication of the scavenging activity which remains in the spent catalyst. However, for purposes of this invention, it is not necessary that any hydrogenation of sulfolene compounds to sulfolane compounds occur during the treatment step.

The hydrogenation of sulfolene compounds to sulfolane compounds after the above-described inventive treatment can be carried out by separating the spent catalyst from the liquid phase using conventional procedures such as filtration, decantation, etc., followed by introduction of fresh hydrogenation catalyst and maintaining the resulting suspension under suitable hydrogenation conditions; or, fresh hydrogenation catalysts can be simply added to the suspension of sulfolene compound, diluent, and spent Raney nickel catalysts with suitable hydrogenation conditions thereafter maintained.

Hydrogenation catalysts which can be used in this invention include any of those known in the art useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals as well as mixtures of these metals with other metals such as iron, zinc, chromium, cadmium, etc. These metals can be used in finely divided form such as, for example, Raney nickel or can be suitably supported on a support such as kieselguhr, aluminum oxide, diatomaceous earth and the like. The catalyst can be charged portionwise or all at once. Generally, 1 to 5 wt. % catalyst based on the amount of sulfolene present is employed.

Suitable hydrogenation conditions are the same conditions of temperature and pressure as given above for suitable treatment conditions. The time employed in the hydrogenation process will generally range from about 30 minutes to about 8 hours, and preferably 1 hour to about 4 hours.

A presently preferred mode of operation follows. The pressure of hydrogen maintained during the hydrogenation process is maintained in the reactor during the following described steps. At the conclusion of the previous sulfolene hydrogenation, stirring and heating are discontinued for a period of about 30 to about 90 minutes, thus allowing the suspended catalyst particles to settle to the bottom of the reactor. Generally, approximately half of the added catalyst will settle to the bottom and the other approximately half will remain in suspension. The supernatant phase containing the diluent, product, and approximately half of the catalyst particles is withdrawn for subsequent recovery procedures. The settled catalyst particles (also containing a small amount of the supernatant phase) are mixed with fresh sulfolene and diluents. Stirring of the suspension is initiated. Following suitable conditions of time and temperature as described above for the treatment step, the catalyst is again allowed to settle. The approximately one-half of the catalyst which settles is withdrawn and discarded. Fresh Raney nickel catalyst is added to the liquid phase with suspended catalyst for the hydrogenation step to proceed. After the desired time has elapsed at appropriate conditions of temperature and pressure for hydrogenation, the stirring and heating is discontinued and the suspended catalyst is allowed to settle. As described above, approximately half of the suspended catalyst settles to the bottom of the reactor and the remainder remains suspended. The settled, spent catalyst is employed in subsequent treatments as described above and the supernatant phase is withdrawn for recovery of desired product. The supernatant phase is filtered to remove suspended catalyst particles followed by suitable fractionation procedures to isolate the desired sulfolane compound.

Since the prior art references, especially U.S. Pat. No. 3,928,385, which is incorporated herein by reference, recognize the benefit of having a tertiary amine present during any heating of sulfolene to inhibit its decomposition and subsequent polymerization of decomposition products, it is usually desirable, though not necessary, to add tertiary amines to the sulfolene compound at the beginning of the treatment process. Such tertiary amines are known in the art to include such examples as trimethylamine, triethylamine, triisobutylamine, methylethylpropylamine, methyldiethylamine, triphenylamine, tribenzylamine, tri-p-tolylamine, tricyclohexylamine, N,N,N',N'-tetramethylethylenediamine, triethylenediamine, hexamethylenetetramine, and the like, and mixtures thereof. Hexamethylenetetramine is presently preferred.

The tertiary amine will generally be employed in an amount in the range of from about 0.001 to about 2 weight percent based on the sulfolene compound to be hydrogenated. The amine can be dissolved in a solvent if desired and can be admixed with the sulfolene feed prior to contacting the feed with the catalysts.

It is also recognized from the prior art that Raney nickel catalyst is preferably employed under basic conditions. Acidic conditions allow the occluded hydrogen on the catalyst surface to be lost. Therefore, it is generally desirable to maintain basic conditions in the treatment process or in the subsequent hydrogenation process by addition, if necessary, of strong base such as sodium hydroxide.

EXAMPLE I

Hydrogenation of crude sulfolene obtained by reaction of butadiene and sulfur dioxide was conducted according to prior art teaching for comparison purposes.

Into a 2 liter reactor were placed hexamethylenetetramine (1 g), fresh Raney nickel (40 g) and a reaction product stream (950 ml) from the reaction of butadiene with sulfur dioxide which stream contained approximately 65 volume percent sulfolene (2- and 3-isomer mixture containing predominantly 3-sulfolene) and approximately 35 volume percent water. (Amounts of sulfur dioxide and polysulfone in the reaction product were not measured.) The reactor was pressurized to 2130 kPa with hydrogen gas and heated at 60° C. with constant stirring. Periodically samples were withdrawn for analysis by vapor phase chromatography. Results recorded in Table I represent the averages obtained from six identical runs.

TABLE I

| Run No. | Reaction Time, Minutes | Analysis[a] | | | |
|---|---|---|---|---|---|
| | | Sulfolene[b] | Water | Sulfolane | Conv., % |
| 1 (prior art) | 30 | 41.9 | 31.3 | 36.6 | 38.7 |
| | 60 | 17.3 | 33.0 | 49.7 | 76.3 |
| | 90 | 1.9 | 33.4 | 64.6 | 97.1 |

[a]Values reported in area percent based on total peaks eluting from gas chromatograph.
[b]As used herein "sulfolene" refers to mixture of 2- and 3-isomers.

It will be observed from the data given in Table I that ninety minutes was an insufficient time period for complete hydrogenation to occur.

EXAMPLE II

The following inventive runs (runs 2-6) were conducted employing treatment of the crude sulfolene described in Example I with a used Raney nickel catalyst prior to hydrogenation using fresh Raney nickel catalyst.

In Run 2 into a 2 liter reactor were placed sulfolene/water solution (950 ml, approximately 35 percent by volume water as described in Example I), hexamethylenetetramine (1 g) and approximately 40 g used Raney nickel catalyst from a preceding sulfolene hydrogenation run. The reactor was pressurized to 2130 kPa with hydrogen and heated at 60° C. with constant stirring. After the time interval specified in Table II, stirring and heating were discontinued, but hydrogen pressure was maintained. The suspension was allowed to settle for 30 minutes after which the supernatant phase containing about half of the original catalyst remaining in suspension was drained into a second 2 liter reactor containing fresh Raney nickel (40 g), water (45 ml), and 0.05 N aqueous sodium hydroxide (2.0 ml). Hydrogen pressure on the second reactor was adjusted to 2130 kPa; the reactor was heated at 60° C. and stirred. Periodically samples were withdrawn for analysis by vapor phase chromatography. The hydrogenation reaction product mixture was passed into a third 2 liter reactor from which approximately one-half of the total suspended catalyst was allowed to settle. The liquid phase was filtered and fractionated to give sulfolane. Results are recorded in Table II.

Runs 3, 4, 5, and 6 were conducted as described for Run 2 except that the settled portion of catalyst remaining in the third reactor was used as the treating agent in each succeeding run. The spent catalyst from Run 4 was allowed to stand open to the air overnight prior to use in the treatment of sulfolene in Run 5. Results are recorded in Table II.

TABLE II

| Run No. | Step of Process | Time, Min. | Analysis | | | |
|---|---|---|---|---|---|---|
| | | | Sulfolene | Water | Sulfolane | Conv., % |
| 2 (Inv) | Treatment | 30 | ND$^a$ | ND | ND | ND |
| | Hydrogenation | 60 | 0.2 | 39.6 | 60.2 | 99.7 |
| | | 115 | —$^b$ | 38.8 | 61.0 | 99.9+ |
| 3 (Inv) | Treatment | 30 | 41.4 | 32.8 | 25.6 | 33.2 |
| | Hydrogenation | 30 | 2.5 | 39.7 | 57.4 | 95.8 |
| | | 45 | 0.2 | 39.5 | 60.3 | 99.7 |
| | | 90 | 0.1 | 39.2 | 60.6 | 99.8 |
| 4 (Inv) | Treatment | 90 | 40.6 | 37.6 | 21.6 | 34.7 |
| | Hydrogenation | 30 | — | 39.4 | 60.6 | 99.9+ |
| | | 60 | 0.1 | 39.8 | 60.1 | 99.8 |
| | | 120 | Tr | 40.4 | 59.6 | 99.9+ |
| 5 (Inv) | Treatment | 30 | 47.2 | 46.5 | 6.3 | 11.8 |
| | Hydrogenation | 15 | 36.7 | 49.2 | 14.1 | 27.8 |
| | | 30 | 28.6 | 50.0 | 21.4 | 42.8 |
| | | 60 | 6.2 | 38.5 | 55.3 | 89.9 |
| 6 (Inv) | Treatment | 30 | 55.4 | 35.3 | 9.3 | 14.4 |
| | Hydrogenation | 30 | 3.0 | 39.2 | 57.8 | 95.1 |
| | | 60 | 0.2 | 39.5 | 60.3 | 99.7 |

$^a$ND = not determined
$^b$— = None detected on chromatogram.

The data in Table II show that a minor amount of hydrogenation occurs during the treatment of sulfolene with spent catalyst; whereas, after addition of fresh catalyst in Runs 2, 3, 4, and 6, hydrogenation proceeded rapidly to a high conversion of sulfolene to sulfolane. The results of Run 5 suggest that exposure of the spent catalyst to air for an extended period before use as a treating agent inhibited the ability of the spent catalyst to function as a treating agent.

In other similar runs which are not described here in detail, results were obtained which show that spent catalyst recovered from larger scale, commercial sulfolene hydrogenation processes was useful in the treatment of sulfolene according to this invention. Furthermore, these runs verified the results of run 5 showing that exposure of the spent catalyst to air inhibited the ability of the spent catalyst to reduce the amount of sulfur dioxide and/or polysulfones in the sulfolene.

We claim:

1. In a process for producing a sulfolane compound wherein a feed comprising a sulfolene compound containing sulfur dioxide and other sulfur-containing catalyst poisons is catalytically hydrogenated in the presence of a hydrogenation catalyst, the improvement comprising pretreating said feed prior to hydrogenation by contacting same in the presence of hydrogen with a used and/or at least partially spent Raney nickel catalyst which contains some degree of scavenging activity under liquid phase conditions and at a temperature in the range of about 10° to about 70° C. and a hydrogen pressure from about 100 to about 7,000 kPa sufficient to substantially remove and/or render innocuous said catalyst poisons.

2. A process according to claim 1 wherein said conditions are substantially the same as the subsequent hydrogenation.

3. A process according to claim 1 wherein at least a portion of the spent catalyst is separated prior to a subsequent hydrogenation.

4. A process according to claim 1 wherein said contacting is carried out additionally in the presence of a tertiary amine compound.

5. A process in accordance with claim 1 wherein said sulfolene compound is selected from the group consisting of compounds having one of the formulas

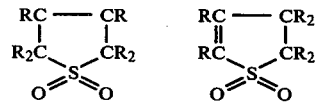

wherein each R is individually selected from the group consisting of hydrogen, hydrocarbon radicals, heterocyclic radicals, inorganic radicals and combinations thereof which do not interfere with the hydrogenation reaction.

6. A process according to claim 1 wherein the hydrogenation catalyst consists essentially of Raney nickel.

7. A process according to claim 1 wherein said Raney nickel catalyst is maintained under an atmosphere of hydrogen between a prior use and said pretreatment to make the catalyst more effective for the removal of catalyst poisons.

8. A process for converting sulfolene to sulfolane which comprises
   (a) pretreating a feed of at least one sulfolene compound containing sulfur dioxide and other sulfur-containing catalyst poisons by contacting same in the presence of hydrogen and a tertiary amine compound with a used and/or at least partially spent Raney nickel catalyst in liquid phase and under conditions sufficient to remove and/or render innocuous said catalyst poisons, (b) separating at least a portion of said spent catalyst from the reaction mixture of (a) leaving a liquid phase of product and some spent catalyst, and (c) contacting the liquid phase of (b) substantially freed of catalyst poisons with active hydrogenation catalysts under conditions which convert said sulfolene compound to sulfolane compound.

9. A process according to claim 8 wherein the pretreatment conditions and the hydrogenation conditions in steps (a) and (c), respectively, are approximately the same.

10. A process according to claim 9 wherein said hydrogenation conditions and pretreatment conditions include a temperature in the range of about 10° to about 70° C. and a hydrogen pressure of from about 100 to about 7,000 kPa.

11. A process according to claim 8 wherein the hydrogenation catalyst in (c) is Raney nickel.

12. A process according to claim 11 wherein said contacting in (a) is carried out in the presence of a tertiary amine compound comprising hexamethylenetetramine.

13. A process according to claim 8 wherein said feed in (a) is a reaction product obtained on reacting a conjugated alkadiene and $SO_2$ and the reaction product contains sulfur-containing poisons detrimental to catalytic hydrogenation catalysts.

14. A process according to claim 8 wherein said separation step (b) comprises the steps of (1) phase separating the reaction mixture of (a) into a spent catalyst phase and a liquid phase containing diluent, product, and some spent catalyst which is withdrawn and (2) adding active Raney nickel catalyst to the liquid phase of (1) and subjecting same to hydrogenation in step (c).

15. A process according to claim 14 comprising the additional steps of (3) adding fresh diluent and sulfolene to said spent catalyst phase in (1) and subjecting same to conditions as defined in step (a) and (4) phase separating the mixture obtained in (3) into liquid phase and a spent catalyst phase which is at least, in part, discarded and then subjecting the remainder to step (2) as set forth in claim 14.

* * * * *